United States Patent
Benalikhoudja

(10) Patent No.: US 9,302,280 B2
(45) Date of Patent: Apr. 5, 2016

(54) TWO-PHASE SPRAYING NOZZLE AND VAPORISING DEVICE COMPRISING SAME

(76) Inventor: Karim Benalikhoudja, Serres Sainte Marie (FR)

( * ) Notice: Subject to any disclaimer, the term of this patent is extended or adjusted under 35 U.S.C. 154(b) by 1102 days.

(21) Appl. No.: 13/381,670

(22) PCT Filed: Jun. 30, 2010

(86) PCT No.: PCT/EP2010/059282
§ 371 (c)(1),
(2), (4) Date: Dec. 30, 2011

(87) PCT Pub. No.: WO2011/000868
PCT Pub. Date: Jan. 6, 2011

(65) Prior Publication Data
US 2012/0104119 A1 May 3, 2012

(30) Foreign Application Priority Data

Jun. 30, 2009 (FR) ..................... 09 03196

(51) Int. Cl.
| | |
|---|---|
| B05B 7/04 | (2006.01) |
| B05B 7/00 | (2006.01) |
| B05B 7/08 | (2006.01) |
| F23D 11/10 | (2006.01) |
| F23D 11/38 | (2006.01) |
| A61M 11/02 | (2006.01) |
| A61M 11/06 | (2006.01) |
| B05B 7/24 | (2006.01) |
| A61M 11/00 | (2006.01) |

(52) U.S. Cl.
CPC ............ *B05B 7/0483* (2013.01); *B05B 7/0012* (2013.01); *B05B 7/0884* (2013.01); *B05B 7/2421* (2013.01); *B05B 7/2424* (2013.01);

(Continued)

(58) Field of Classification Search
CPC .. B05B 7/0884; B05B 7/0012; B05B 7/2405; B05B 7/2421; B05B 7/2408; B05B 7/2424; B05B 7/0883; B05B 7/0425; F23D 11/101; F23D 11/102; F23D 11/38; F23D 11/10
USPC ................ 239/398, 400, 427.3, 427.5, 434
See application file for complete search history.

(56) References Cited

U.S. PATENT DOCUMENTS

| 4,160,526 A * | 7/1979 | Flanagan ................. 239/427 |
| 4,348,168 A * | 9/1982 | Coulon ..................... 431/9 |

(Continued)

FOREIGN PATENT DOCUMENTS

| DE | 26 27 880 A1 | 12/1977 |
| DE | 10 2006 001319 A1 | 7/2007 |

(Continued)

OTHER PUBLICATIONS

International Search Report, dated Sep. 21, 2010, from corresponding PCT application.

(Continued)

*Primary Examiner* — Arthur O Hall
*Assistant Examiner* — Viet Le
(74) *Attorney, Agent, or Firm* — Young & Thompson

(57) ABSTRACT

The vaporization nozzle (1) is formed by a nozzle body (10) including a first pressurized gas intake perforation (11), and at least one second perforation (12) for intake of a liquid to be fractionated, in communication with the first perforation, and a liquid vaporization zone (13), formed in the axis of the first perforation (11). This nozzle is noteworthy in particular in that the or each intake perforation (12) of the liquid is in communication with the first perforation (11) through an underpressure chamber (15) that is formed between the first perforation and the vaporization zone, with the propellant gas stream passing all the way through the depression chamber (15).

20 Claims, 12 Drawing Sheets

Figure 1:
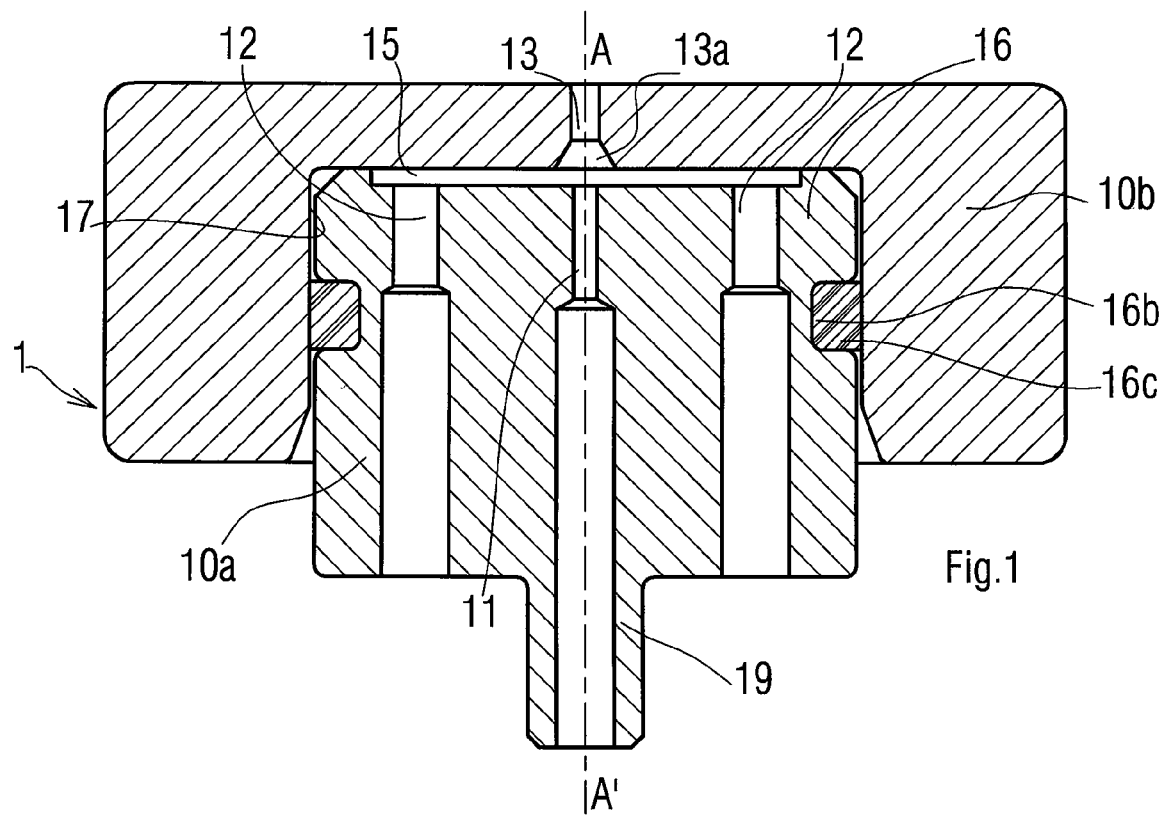

(52) U.S. Cl.
CPC .............. *F23D 11/102* (2013.01); *F23D 11/38* (2013.01); *A61M 11/001* (2014.02); *A61M 11/02* (2013.01); *A61M 11/06* (2013.01); *B05B 7/0425* (2013.01); *B05B 7/2408* (2013.01)

(56) References Cited

U.S. PATENT DOCUMENTS

| 5,337,962 A | 8/1994 | Erb et al. |
|---|---|---|
| 2008/0283049 A1 | 11/2008 | Mahoney et al. |
| 2009/0050141 A1 | 2/2009 | King et al. |

FOREIGN PATENT DOCUMENTS

| EP | 0 101 109 A2 | 2/1984 |
|---|---|---|
| FR | 972 990 A | 2/1951 |
| FR | 2 700 482 A1 | 7/1994 |
| GB | 552 689 A | 4/1943 |

OTHER PUBLICATIONS

"Hybrid Aerated Liquid Atomizer", Research Disclosure, Mason Publications, Oct. 1, 1993, p. 686, XP-000412838.

* cited by examiner

TWO-PHASE SPRAYING NOZZLE AND VAPORISING DEVICE COMPRISING SAME

TECHNICAL FIELD

This invention is of the field of equipment used for diffusing an aerosol of fine liquid particles into the atmosphere, and it relates more particularly to a two-phase nozzle for spraying a liquid and a vaporization device that is equipped with a nozzle according to the invention.

It should be recalled that vaporization should be understood as an operation whose purpose is the formation of an aerosol whose liquid particle size is less than 5 μm.

PRIOR ART

Typically, the two-phase spraying nozzles comprise a body in which the following are formed: a first intake perforation for a carrier gas, and a second intake perforation for the liquid to be sprayed, in communication with a liquid reservoir and a fractionation chamber in communication with the two perforations in which the liquid is divided into fine droplets by the carrier gas. This chamber has an outlet opening of a spray jet formed by liquid particles in suspension in a stream of carrier gas. In general, these nozzles use the Venturi effect so that under the action of the flow rate of the propellant gas, the liquid to be sprayed is drawn into the fractionation chamber. These nozzles generally are not designed to form particles of calibrated sizes; on the contrary, they use a geometry and a jet that allows wide variability in size of the latter. Thus, the size of these particles can be between 0.2 μm and 10 μm.

For the purpose of the formation of a vaporization, this nozzle is functionally associated with an expansion and trapping chamber whose essential function is to ensure a dimensional sorting of the liquid particles so that an aerosol, a majority of which consists of particles with sizes less than a determined caliber, is delivered to the chamber outlet. The particles with sizes larger than this caliber are captured in the chamber by various means and return in the form of a residual flow toward a liquid reservoir that is functionally associated with the spraying nozzle. The functional unit that consists of a nozzle and a vaporization chamber is commonly called "vaporization head."

These vaporization heads make it possible, most often in cases based on the nature of the liquid, to diffuse into an ambient atmosphere an odorous substance, for example a perfume, an insecticide, or else even a disinfectant for bacteriological decontamination of the air and of the surfaces of the premises. They can also be used for vaporization curative substances for therapeutic purposes, for example for the treatment of respiratory passages of patients in aerosol therapy, or else for veterinary purposes, for example for the vaccination of farm animals.

They can also be used for the formation of a mixture, in the form of a spray, of a liquid fuel with a fuel gas for the purpose of supplying thermal machines.

From the Patent Application FR 2 700 482, a micro-diffuser for a liquid particle spray, equipped with a spraying nozzle comprising an open spraying chamber in which a stream of pressurized propellant gas and a stream of liquid to be fractionated are simultaneously introduced through suitable jets, is known. Because of the position of the jets, one relative to the other, and of the flow rate of the propellant gas, an underpressure is created downstream from the liquid output jet. Under the action of this underpressure, the liquid, by Venturi effect, is drawn into the fractionation chamber and is divided there into fine particles by the pressurized propellant gas.

The fractionation chamber is in the shape of a truncated cone, and the two jets are provided at the base of the latter: one, that of the propellant gas, in an axial manner, and the other, that of liquid, in a radial manner.

The vaporization chamber that comprises the micro-diffuser according to this patent application has a series of baffles that can trap the large particles.

A device for spraying or vaporization that implements a spraying nozzle comprising a nozzle body, in which there are formed a first axial perforation that empties out into an upper opening and second perforations that are lateral to the axial perforation, connected to the latter by coplanar, radial pipes, with each side perforation and the associated radial channel forming a liquid intake pipe in communication with a liquid reservoir, is also known from the Patent Application GB 552 689. The axial perforation is provided for accommodating a pressurized air flow under the action of the displacement speed from which an underpressure is formed in the radial channels, and the liquid is drawn in and next fractionated and driven by the stream of pressurized air to the upper opening. The thus formed liquid particle jet is introduced into a vaporization chamber and in the latter strikes the wall of a discharge tube. This arrangement ensures the trapping of large liquid particles.

DISCLOSURE OF THE INVENTION

Technical Problem

The two-phase nozzles that are dedicated to vaporization, known from the state of the art, have a certain number of drawbacks. In particular, instability of the jet formed and a poor yield were observed for most of them.

The instability of the jet results essentially either from an unbalanced supply of liquid and/or from an irregular supply flow. For the nozzle according to the Patent Application FR 2 700 482, the radial position of the liquid intake causes an asymmetry of the jet that is formed with a non-uniform distribution of particles whereas the latter should be perfectly conical. For the nozzle according to GB 552 689, the partial or total blockage of one of the liquid intake perforations can be reflected by an imbalance of the jet and by an irregular or erratic fractionation of the liquid.

The poor yield of the nozzle essentially results from too small a proportion, only on the order of 15%, of particles with suitable sizes, namely less than 5 μm.

To compensate for low yields, it is known to increase the flow rate of the carrier stream through the nozzle and for this reason to use oversized air compressors relative to the desired application. This is reflected by increased energy consumption.

Another drawback of the two-phase nozzles of the prior art sticks to the fact that it is difficult to control the intake level because of their configuration, which does not allow constant and suitable underpressure to be reached.

Also, another drawback of the current nozzles sticks to the fact that they cannot be reproduced because of their geometric profiles that are extremely difficult to produce and to monitor. This defect is reflected, from one nozzle to the next, by dispersions of results in terms of spraying quality. To eliminate this drawback, the jet point position between the air and liquid intakes may be adjustable but this implementation operation is difficult to control, considering the narrowness of the size ranges involved. In addition, it happens that the initial adjustments are altered over time under the action in particular of wear and tear and vibrations that the nozzle undergoes primarily during its operation. Modifications of behavior detrimental to a good yield follow.

Finally, the known nozzles cannot produce a jet of particles in an extended flow range.

Technical Solution

This invention has as its object to solve the drawbacks cited above by implementing a nozzle that can produce a perfectly conical, homogenous and perfectly stable jet.

Another object of this invention is the implementation of a nozzle that has a good yield.

Another object of this invention is a nozzle design with which a reproducibility of the results is achieved from one nozzle to the next.

Another object of this invention is the implementation of a nozzle for which no adjustment is required.

For this purpose, the spraying nozzle according to the invention, formed by a nozzle body comprising a first pressurized gas intake perforation that has an inlet opening and an outlet opening, at least one second perforation for intake of a liquid to be fractionated that has an inlet opening and an outlet opening, and a liquid fractionation zone, axially aligned with the first perforation along a geometric AA' axis, whereby said fractionation zone is in communication with the first and second perforations, is characterized essentially in that it comprises several liquid intake perforations, and in that each of these perforations is in communication with the first perforation and with the fractionation zone through the same underpressure chamber formed between said first perforation and the fractionation zone, whereby the propellant gas stream passes through said underpressure chamber and whereby the diameter of the fractionation zone is larger than the diameter of the first perforation at its opening into the underpressure chamber.

Under the action of the speed of the propellant gas, by Venturi effect, an underpressure is created in the underpressure chamber, and the liquid to be sprayed is drawn in toward the latter. Because of the presence of this chamber, which constitutes a liquid buffer reserve, the regularity of the flow rate of the spray jet at the nozzle outlet is ensured.

Such a nozzle has the advantage of a manufacturing process that is particularly simple and easy to monitor and totally reproducible without any adjustment.

In addition, this nozzle can be produced in plastic injection technologies so as to optimize the manufacturing costs and to be able to be integrated in disposable vaporization cartridges.

Because of the presence of the underpressure chamber, the underpressure that is achieved is relatively significant, taking into account the speed of the propellant gas jet in such a way that for the pressurization of this gas, a lower-power compressor can be used.

Purely by way of indication with a micro-compressor operating under a 12 Vcc voltage and able to produce a carrier gas jet under a pressure of 250 mbar, a liquid will be drawn in on a level of 1 meter. For vaporization applications, the suction of liquid with a micro-compressor that operates under 12 Vcc is 20 mbar over an underpressure level of 160 mm.

According to another characteristic of the invention, the jet of the first perforation at the opening of the latter in the underpressure chamber is axial to said chamber, and the jets of the second perforations at the openings of the latter in said chamber are arranged symmetrically relative to the AA' axis.

According to another characteristic of the invention, the flow rate of liquid by spraying or by vaporization is adjustable by increasing the volume of the underpressure chamber or by multiplying the number of liquid intake openings in the chamber, this selection being determined by the installation of the nozzle on its support. Such an arrangement offers the advantage of a high flexibility in its installation.

This arrangement of balanced distribution of jets makes possible the homogenous supply of liquid of the fractionation zone and consequently the formation of a perfectly conical and homogeneous jet.

According to another characteristic of the invention, the volume of the underpressure chamber is adjustable. It is thus possible to adjust the volume of the liquid buffer but also for a given propellant gas flow rate, with the value of the underpressure prevailing in this chamber and consequently the flow rate of the liquid that is drawn in.

According to another characteristic of the invention, the adjustment of the volume of the underpressure chamber is operated by variation of the level of the latter.

According to another characteristic of the invention, the nozzle body is formed by two parts that are sealed to one another between which the underpressure chamber is formed, with the level variation of the latter, according to another characteristic of the invention, being operated by axial movement of the two parts relative to one another.

According to another characteristic of the invention, the fractionation zone is formed by a perforation that empties out into the underpressure chamber and into the axis of the first perforation.

According to another characteristic of the invention, the perforation that constitutes the fractionation zone has a conical widening at its opening in the underpressure chamber and facing the first perforation. This arrangement has the effect of increasing the efficiency of the fractionation of the liquid and of placing the underpressure chamber under vacuum.

According to another characteristic of the invention, the nozzle body, radially to the spray jet, can accommodate a tube that has at least two air intakes that empty out opposite the liquid spraying outlet, whereby said air intakes are uniformly distributed around the axis of symmetry.

This arrangement, by Venturi effect, makes possible an introduction of air into the jet that is produced so as to increase its air flow at the nozzle outlet.

This invention also relates to a device that comprises at least one nozzle according to the invention.

According to another characteristic of the invention, the device comprises a hollow hardware body that is equipped with an end fitting on the collar of a liquid reservoir, a transverse base arranged above the end fitting in which at least one housing is formed that can accommodate a spraying nozzle in nested form.

SUMMARY DESCRIPTION OF THE FIGURES AND DRAWINGS

Figure 1A:
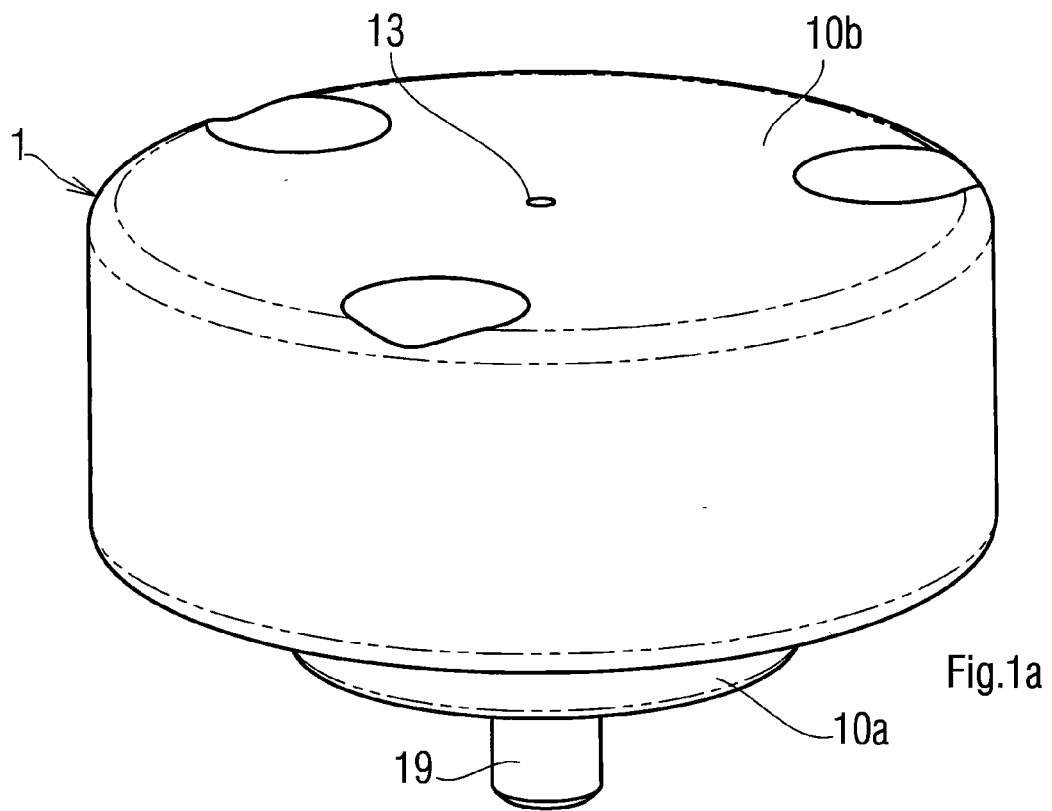
Figure 2:
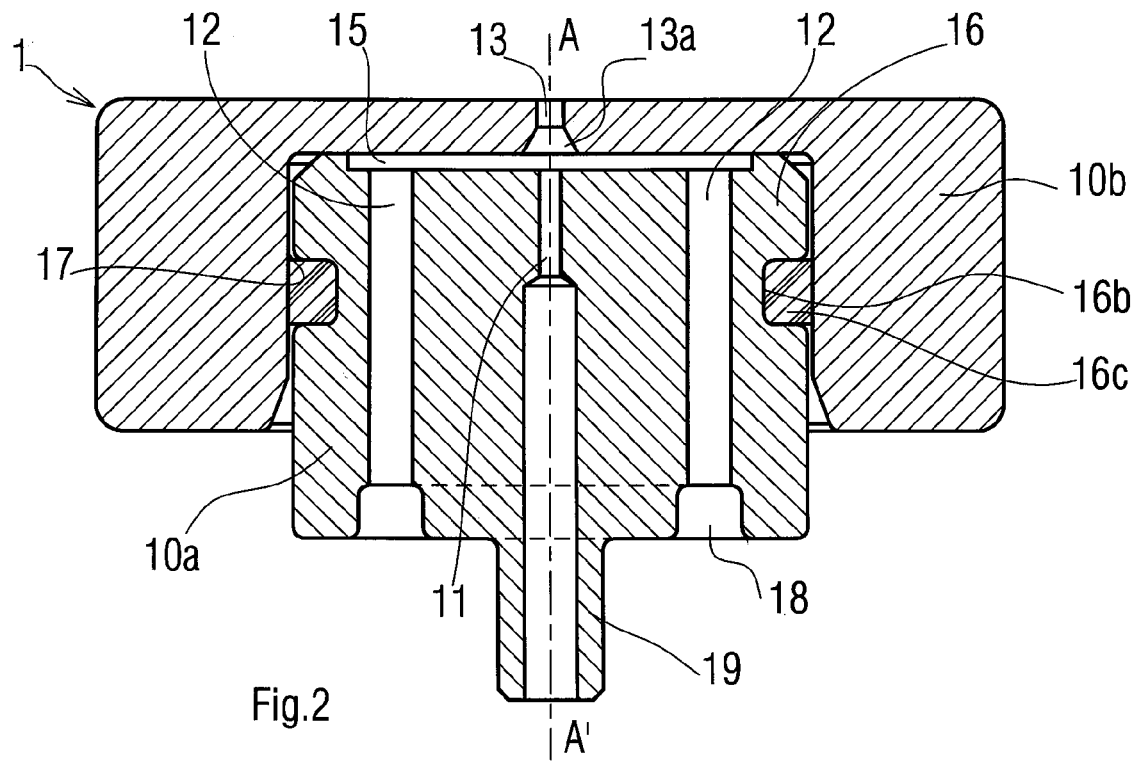
Figure 2A:
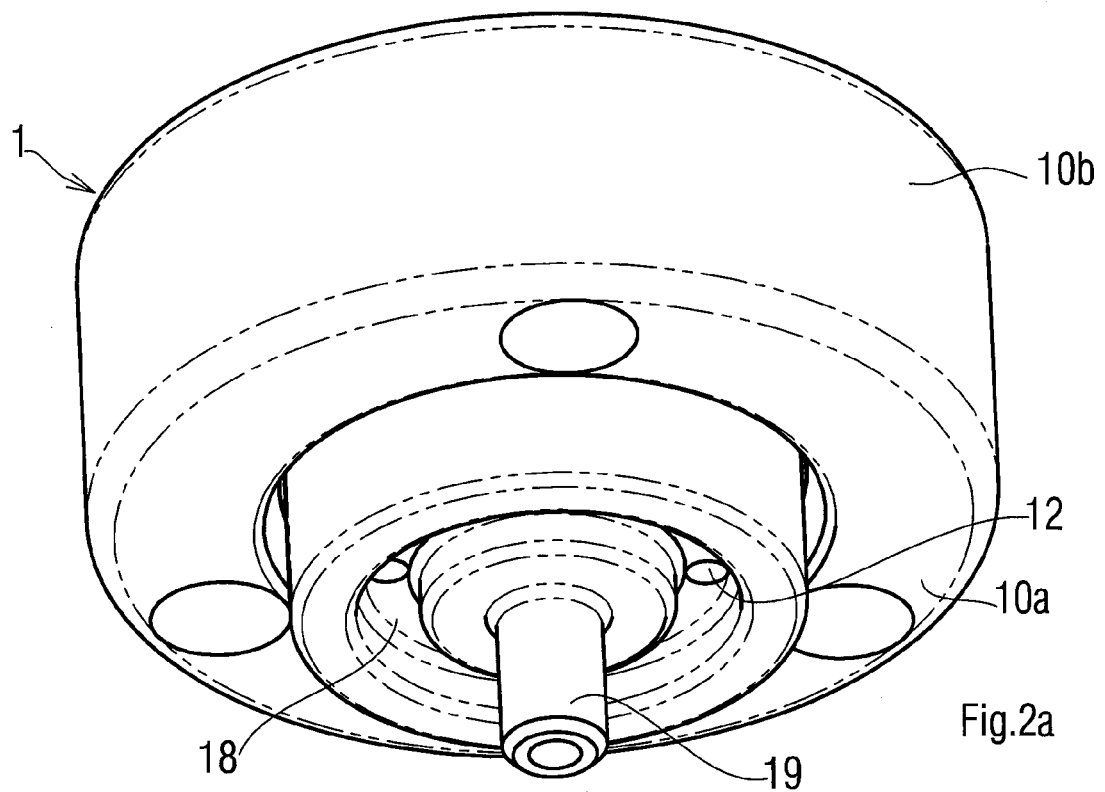
Figure 3:
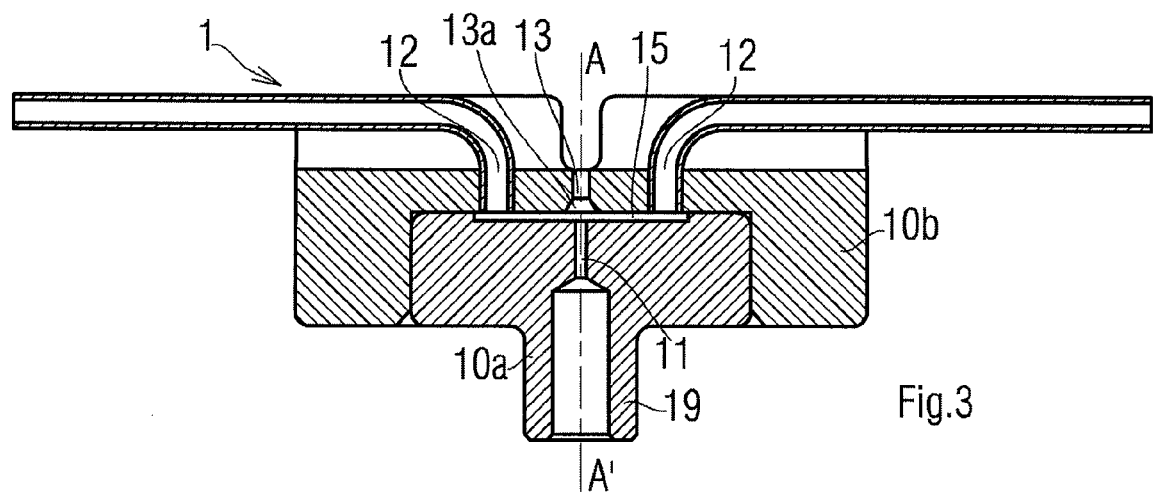
Figure 3A:
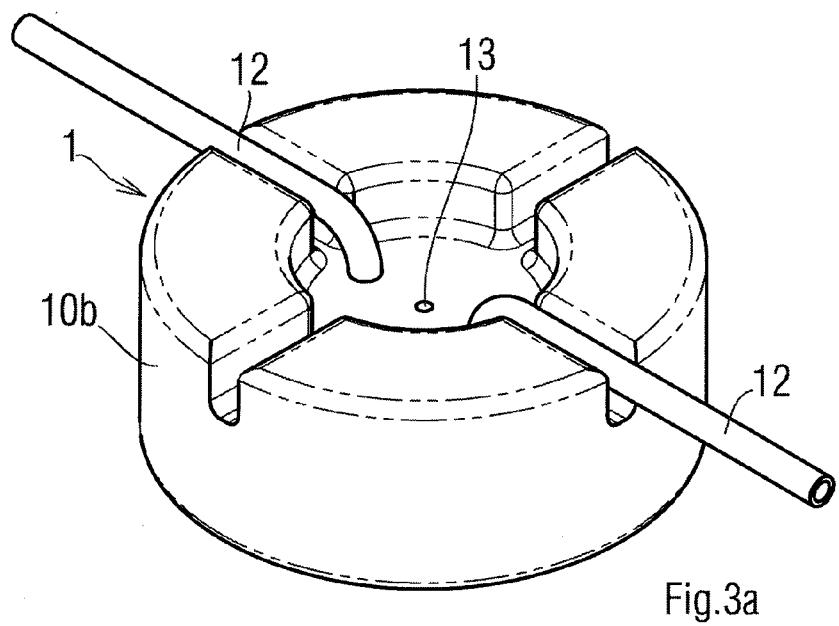
Figure 4:
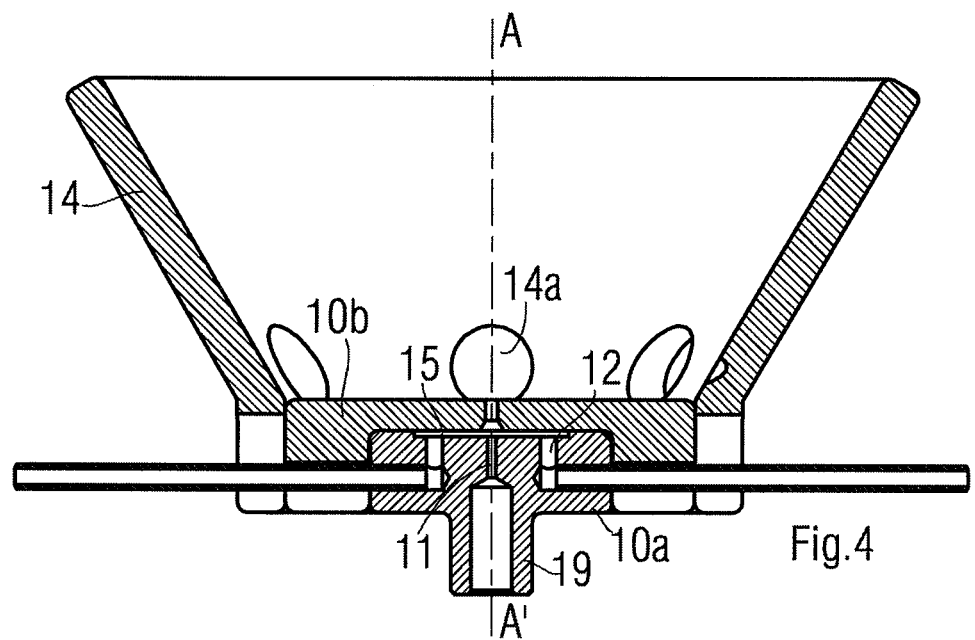
Figure 4A:
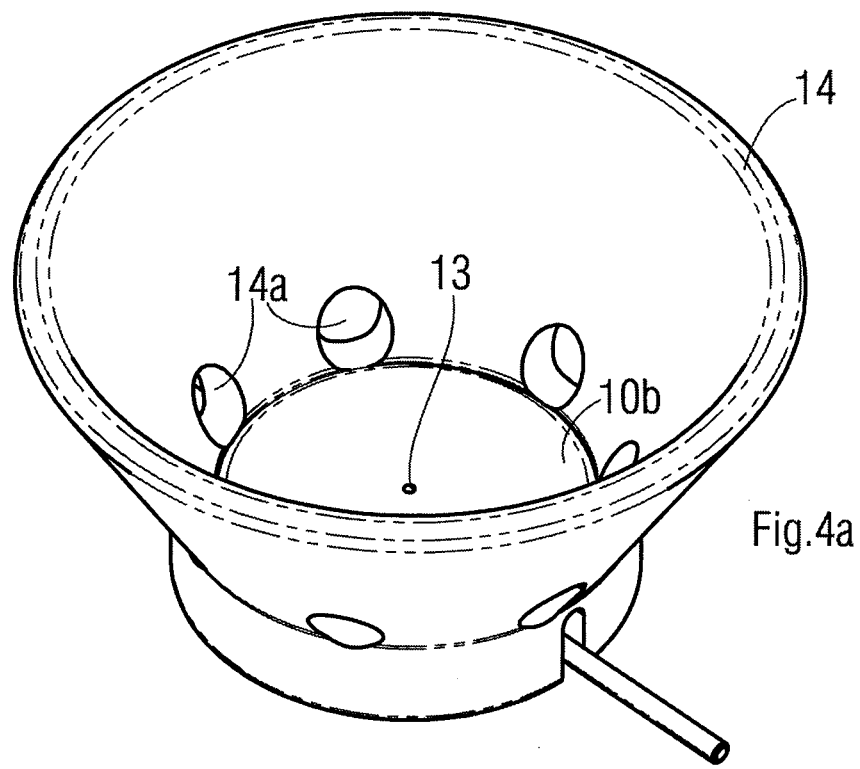
Figure 5:
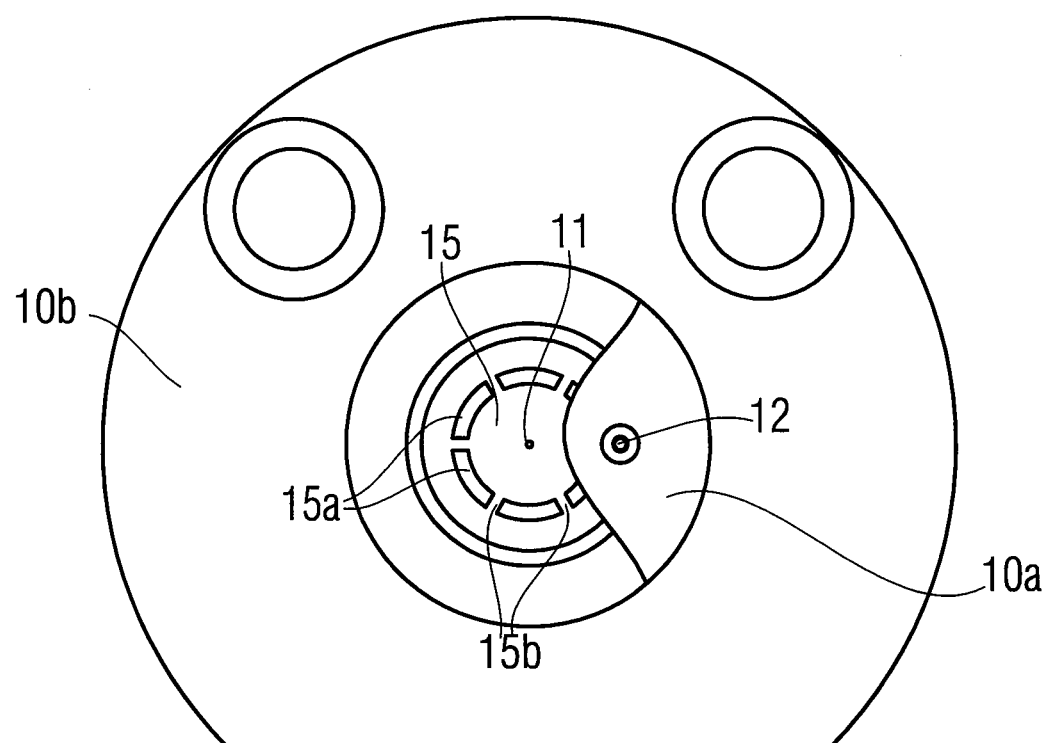
Figure 5A:
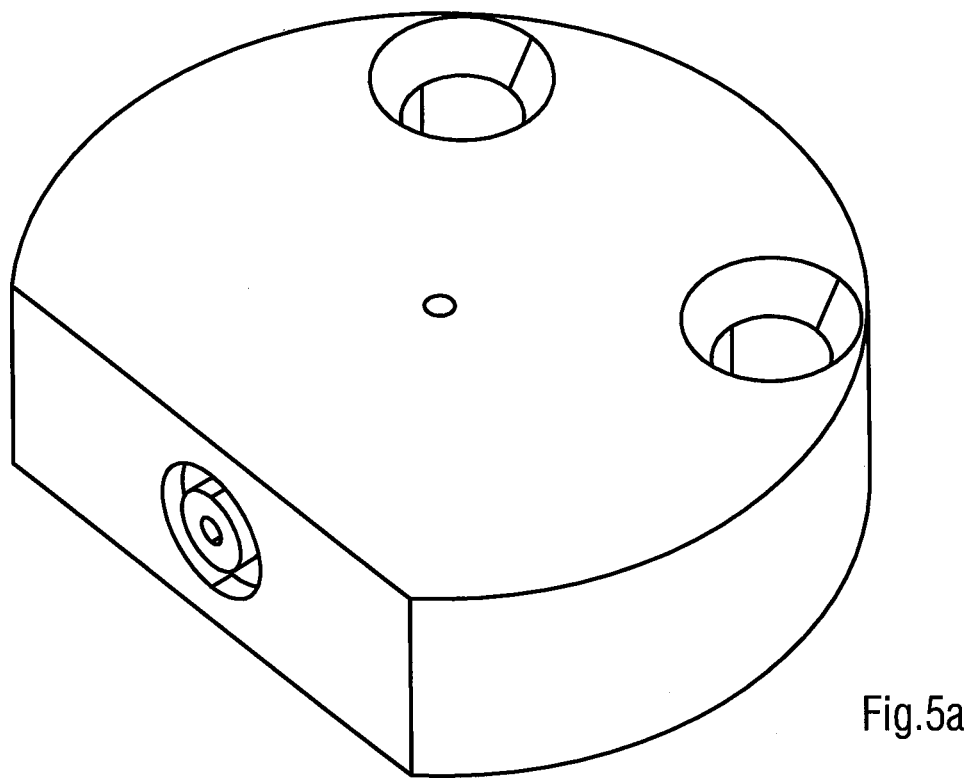
Figure 6:
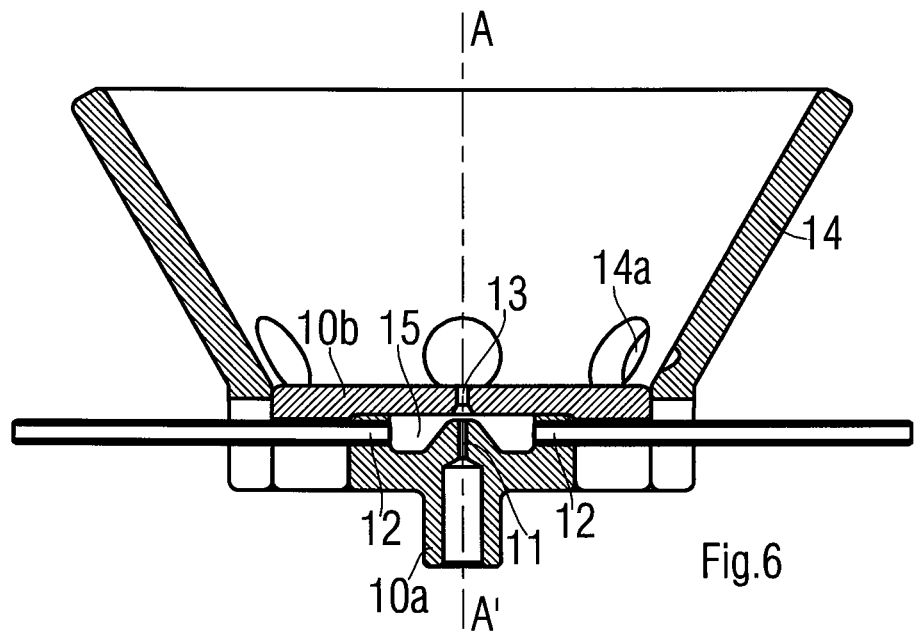
Figure 6A:
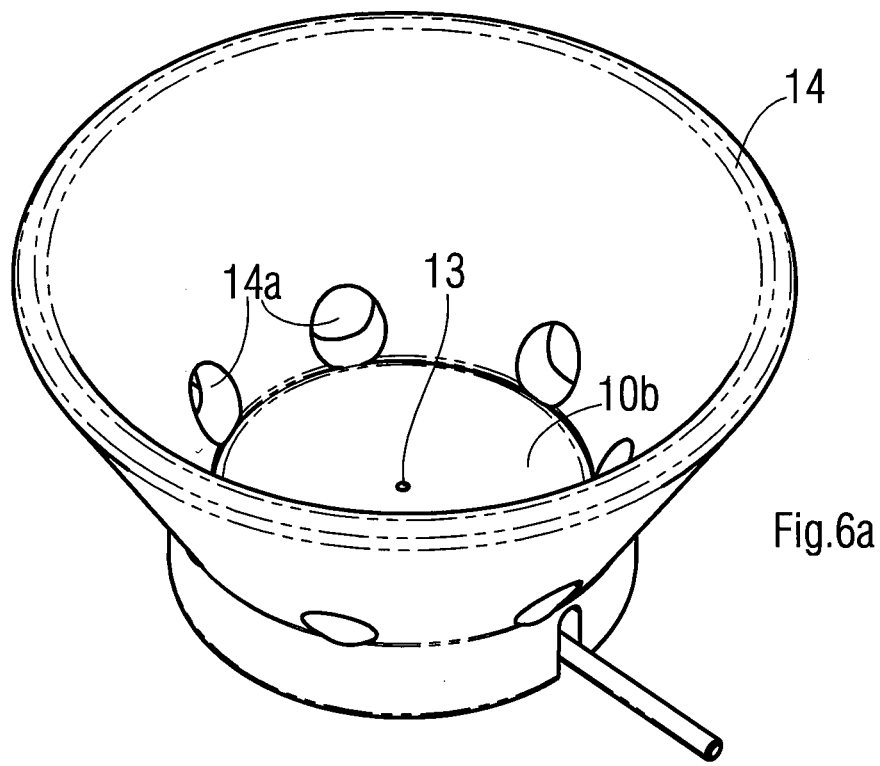
Figure 7:
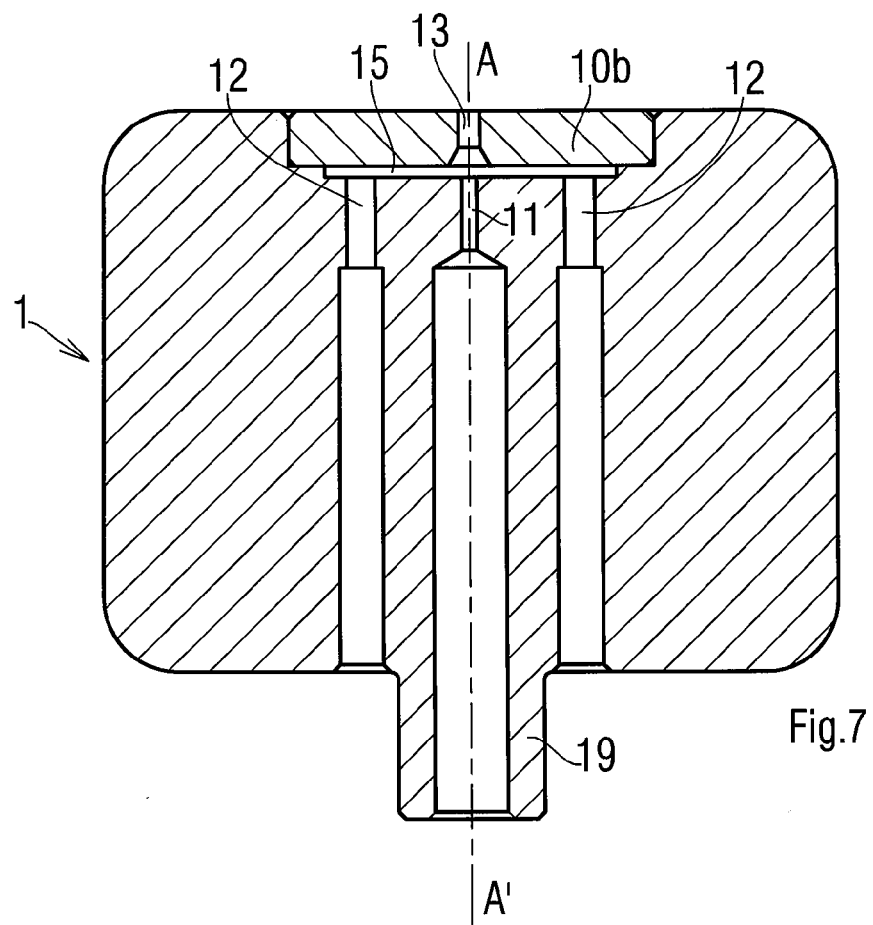
Figure 7A:
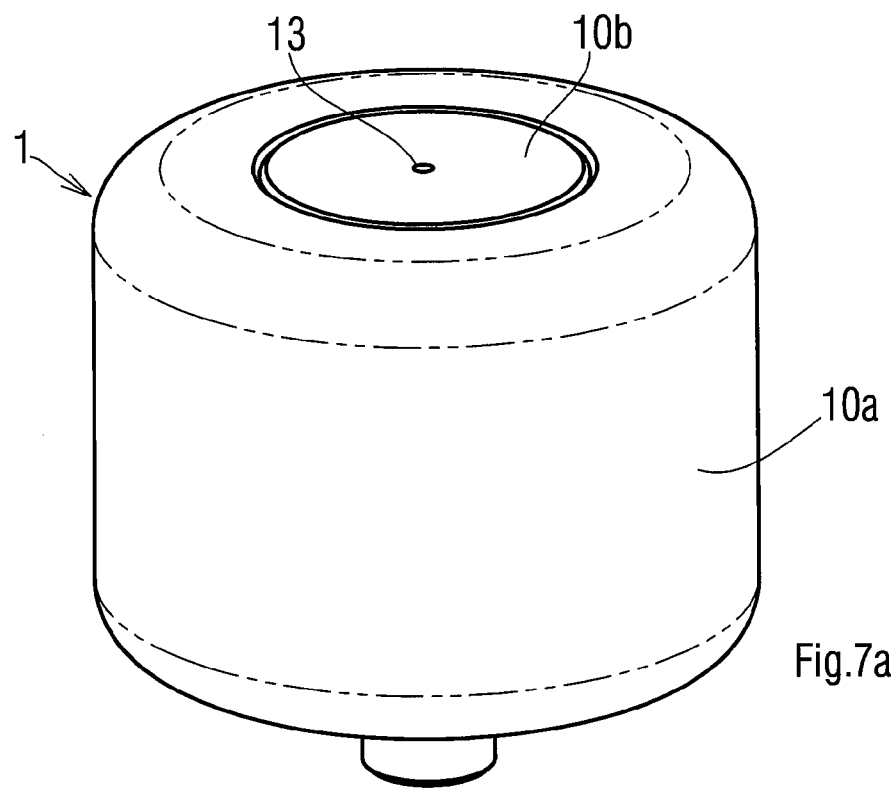
Figure 8:
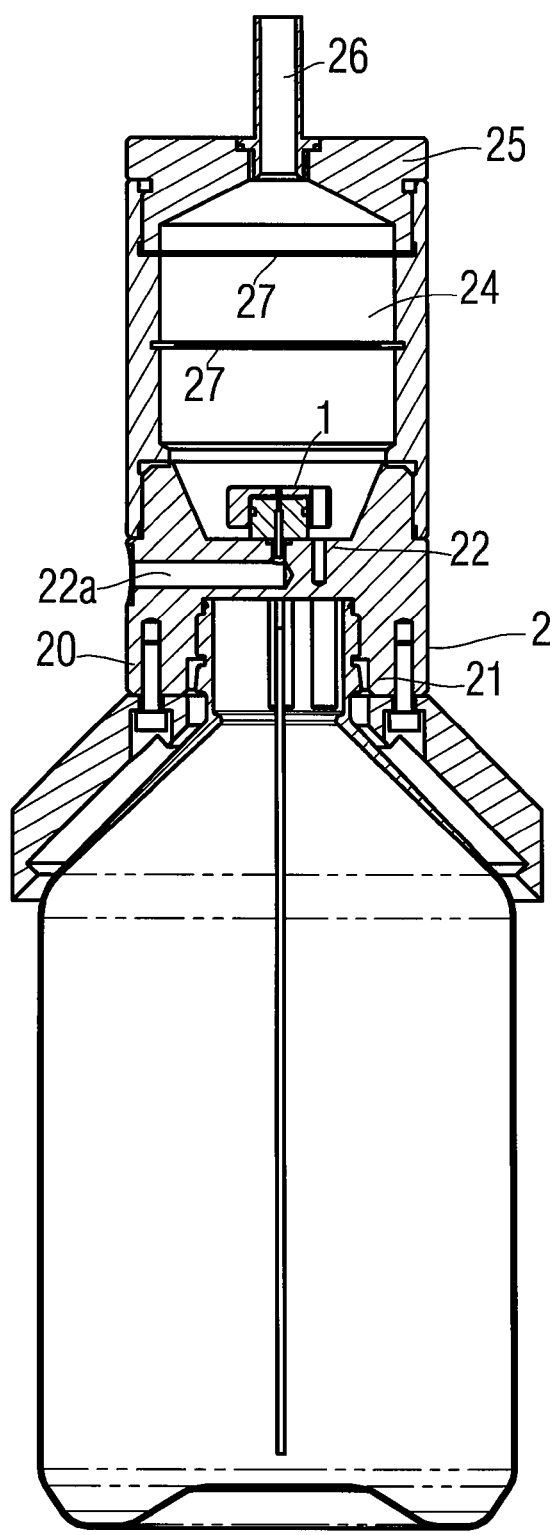
Figure 8A:
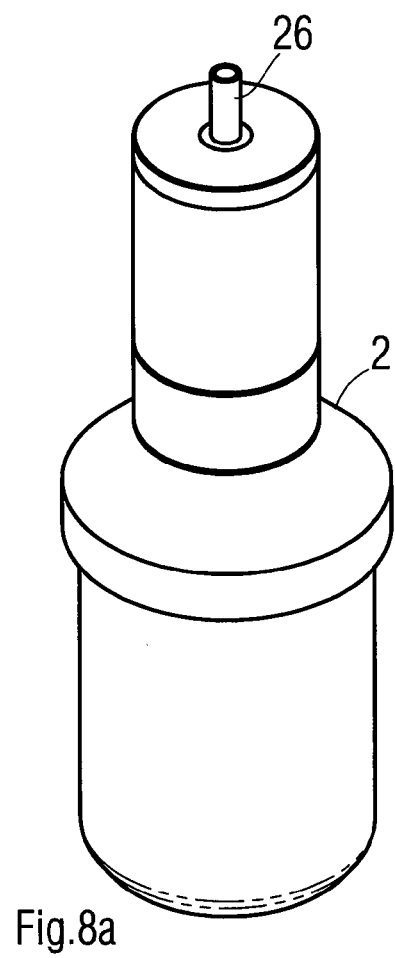
Figure 9:
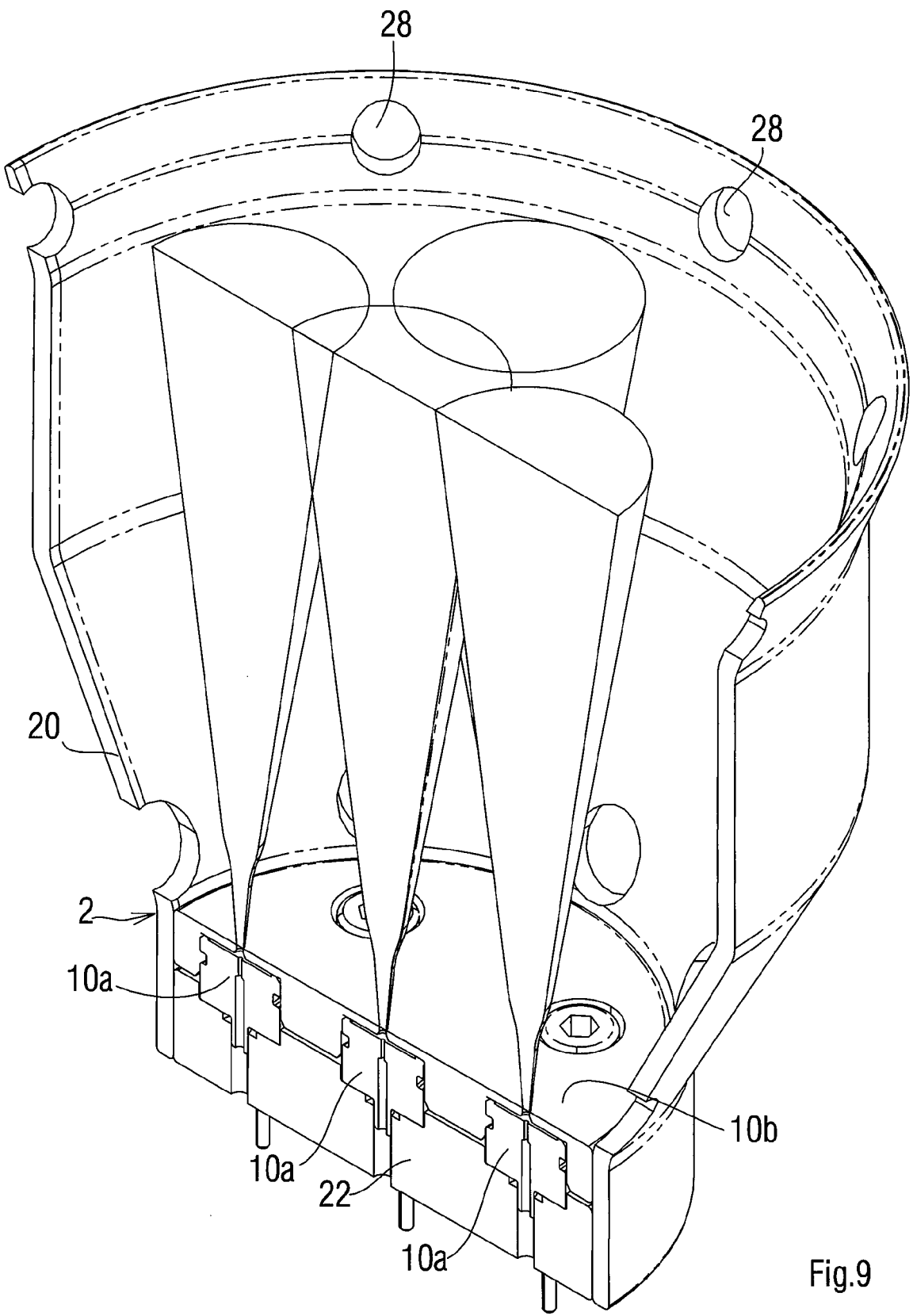
Figure 10:
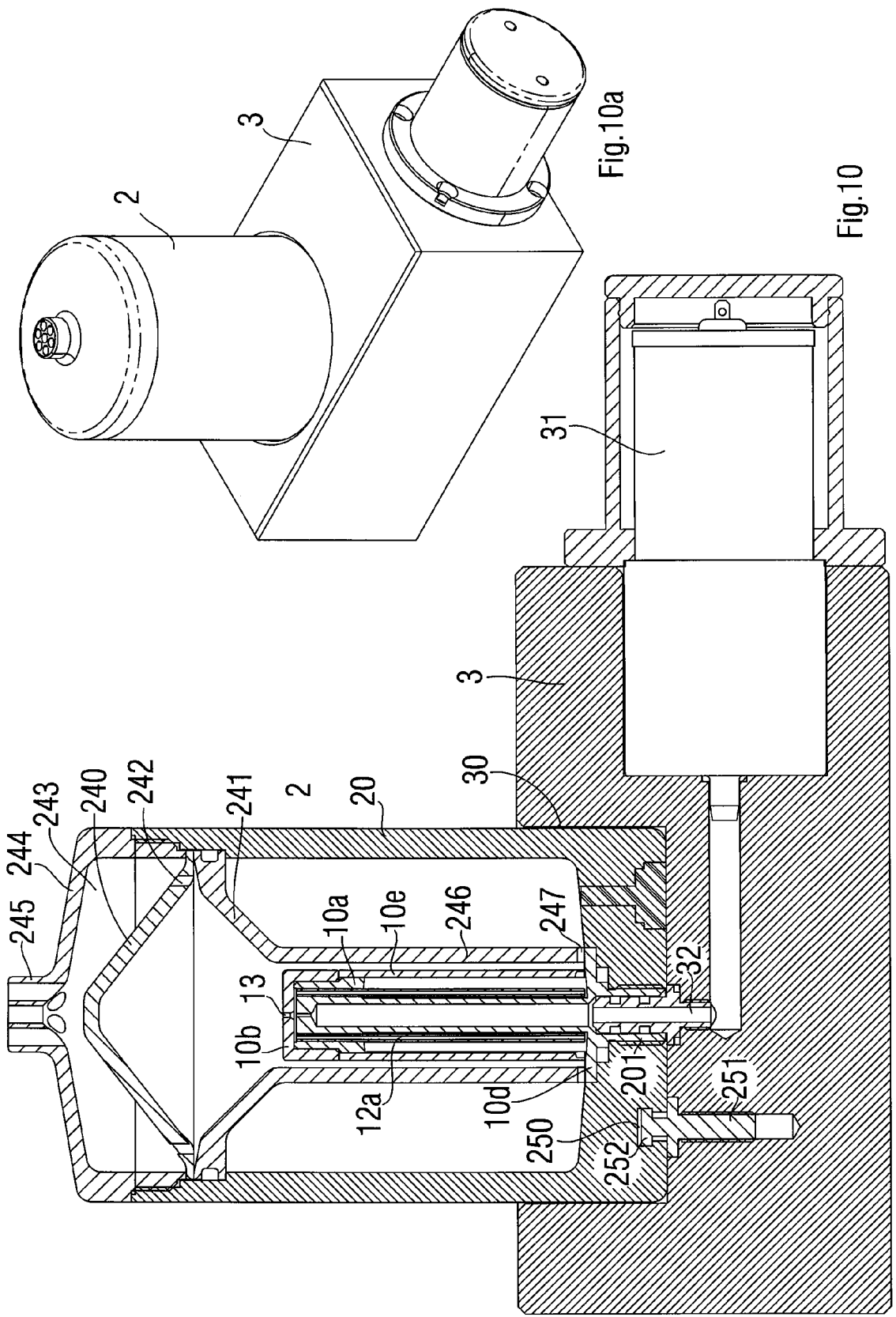
Figure 11:
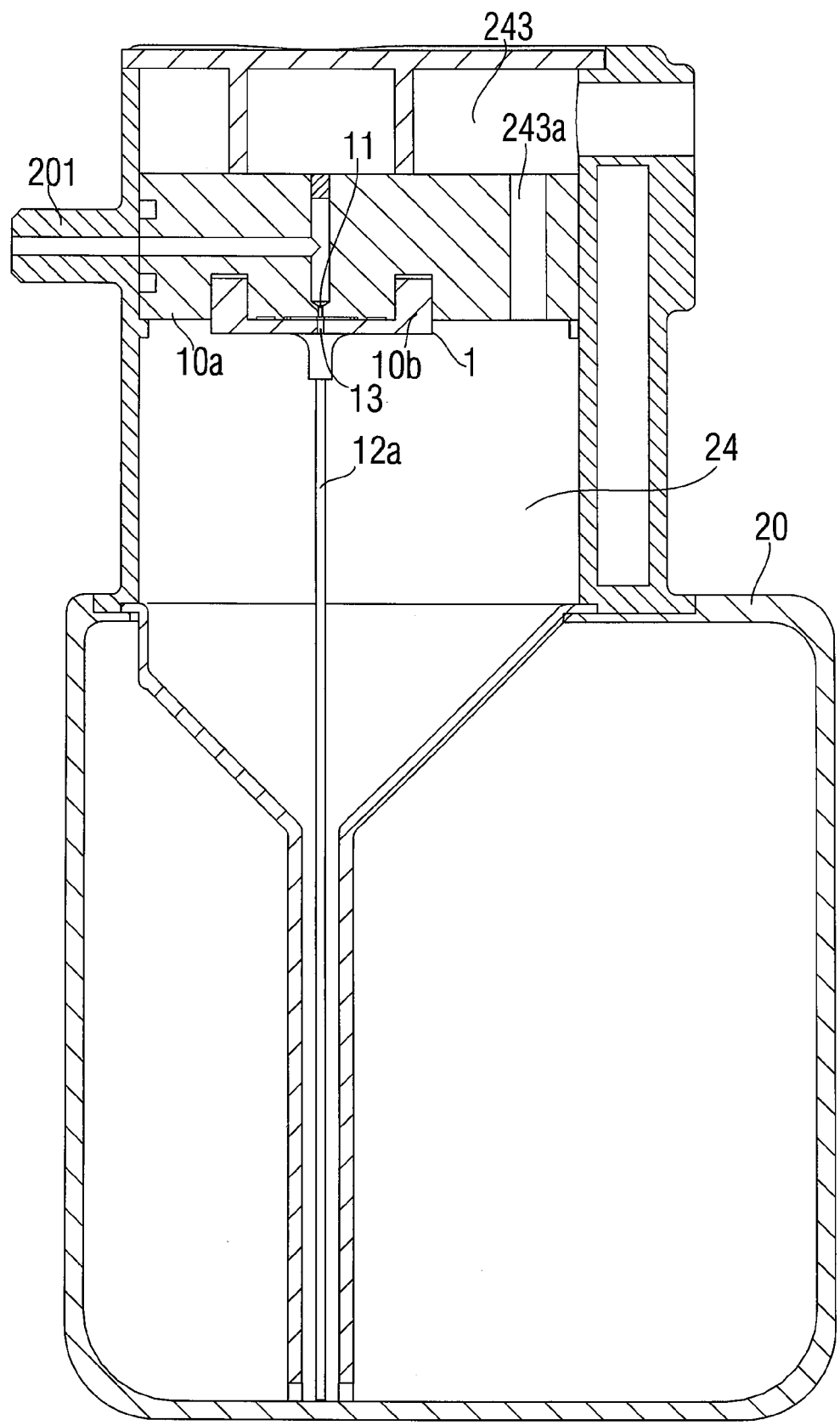
Figure 11A:
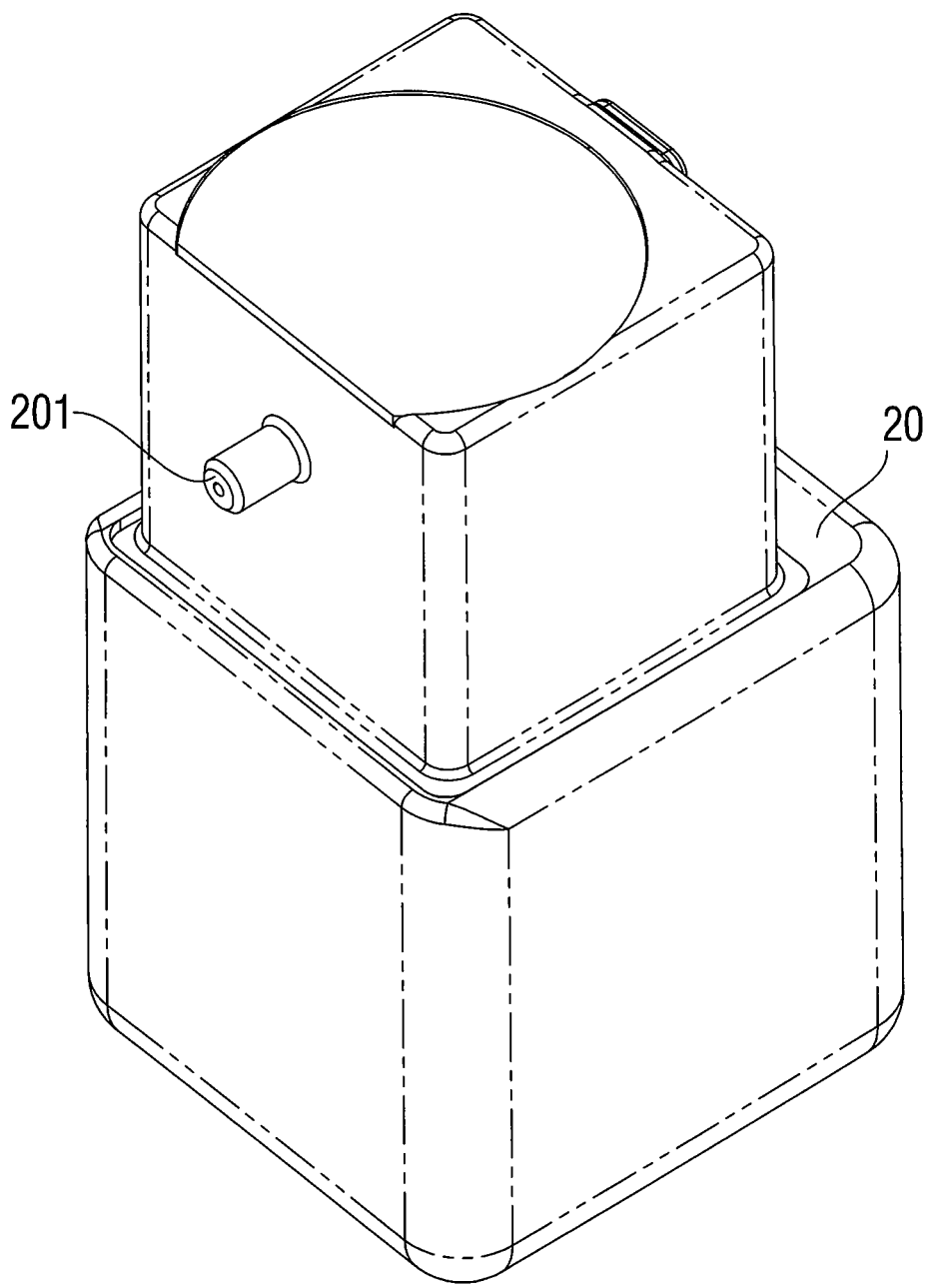

Other advantages, objects and characteristics of the invention will emerge from reading the description of a preferred embodiment, provided by way of nonlimiting example with reference to the accompanying drawings in which:

FIG. 1 is a longitudinal cutaway view of a nozzle according to a first embodiment, FIG. 1a is a perspective view of a nozzle according to FIG. 1, FIG. 2 is a longitudinal cutaway view of a nozzle according to a second embodiment, FIG. 2a is a perspective view of a nozzle according to FIG. 2, FIG. 3 is a longitudinal cutaway view of a nozzle according to a third embodiment, FIG. 3a is a perspective view of a nozzle according to FIG. 3, FIG. 4 is a cutaway view of a nozzle according to a fourth embodiment, FIG. 4a is a perspective view of a nozzle according to FIG. 4, FIG. 5 is a cutaway plan view of a nozzle according to another embodiment, FIG. 5a is a perspective view of the nozzle according to FIG. 5, FIG. 6 is a longitudinal cutaway view of a nozzle according to another embodiment, FIG. 6a is a perspective view of a nozzle according to FIG. 6, FIG. 7 is a longitudinal cutaway view of a nozzle according to another embodiment, FIG. 7a is a perspective view of a nozzle according to FIG. 7, FIG. 8 is a longitudinal cutaway view of a device that comprises a nozzle according to the invention, FIG. 8a is a perspective view of a device according to FIG. 8, FIG. 9 is a partial, cutaway perspective view of a device that is equipped with several vaporization nozzles, FIG. 10 is a cutaway view of a device according to another embodiment, installed on a support, FIG. 10a is a perspective view of the device according to FIG. 10, FIG. 11 is a cutaway view of a device according to another embodiment, FIG. 11a is a perspective view of the device according to FIG. 11.

BEST WAY TO IMPLEMENT THE INVENTION

As shown in FIGS. 1 to 7, the nozzle according to the invention is formed by a preferably cylindrical rigid nozzle body, in which the following are formed: a first perforation 11, axial to the body, of an intake of a pressurized propellant gas, with this first perforation having an inlet opening and an outlet opening, and several second perforations 12 for intake of a liquid to be fractionated, whereby each second perforation has an inlet opening and an outlet opening and a liquid fractionation zone 13, axially aligned with the first perforation along a preferably rectilinear geometric AA' axis, with said fractionation chamber being in communication with the first and second perforations.

In accordance with the invention, the nozzle 1 is equipped with an underpressure chamber 15 that is formed between the first perforation 11 and the fractionation zone 13, whereby the propellant gas stream passes through this chamber 15, and this chamber is supplied with liquid through the second perforations 12, with the first perforation 11 and second perforation 12 emptying out into said chamber by the outlet opening thereof. As can be seen in the different figures, the underpressure chamber 15 comprises a lower surface in which the outlet opening of the air intake perforation 11 is formed, with an upper surface opposite the preceding one into which the fractionation chamber 13 empties out and with one or more lateral surfaces developing between the lower and upper surfaces.

In accordance with the invention, the outlet openings of the second perforations 12 are arranged symmetrically relative to the geometric AA' axis, and said AA' axis is central to said underpressure chamber 15. This arrangement ensures a uniform and balanced supply of the underpressure chamber and the fractionation zone.

According to a first embodiment, as shown in FIGS. 1 to 5 and 7, the second perforations 12 are lateral and parallel to the first perforation 11 and are distributed uniformly around the latter. In this embodiment, the outlet openings of liquid intake perforations 12 are formed in the lower surface of the underpressure chamber (FIGS. 1, 2, 4, 5 and 7) or on the upper flat surface of said chamber (FIG. 3).

According to another embodiment as can be seen in FIG. 6, the outlet openings of the liquid intake pipes are formed in the lateral surface(s) of the underpressure chamber 15. In this embodiment, the lower surface of the underpressure chamber will comprise an annular hollow recess formed around an axial projection that accommodates the carrier gas intake perforation 11, with the outlet opening of each liquid intake perforation 12 being formed in the corresponding lateral surface of the annular recess.

The underpressure chamber 15 as can be seen more particularly in FIG. 5 can be equipped with an annular partition 15a, centered relative to the AA' axis, occupying its entire height and dividing it into a central volume through which the carrier gas stream passes and a peripheral annular volume into which the liquid intake perforations 12 empty out. This annular wall is provided with radial perforations 15b that ensure the communication between the annular volume and the central volume. Such an arrangement makes it possible to create controlled loss of feedstock and is suitable for a low-pressure application of the nozzle. In addition, it makes possible a better balancing of the liquid intake. In addition, for a synthetic nozzle, the annular wall consists of a rigid support that prevents any deformation of the upper part.

Advantageously, the underpressure chamber 15 is cylindrical in shape, but, as a variant, this chamber can be parallelepipedic.

The volume of the underpressure chamber 15 is preferably adjustable by variation of its height. The adjustment of the volume of the chamber besides the fact of adjusting the quantity of liquid that it can allow makes it possible to adjust the degree of underpressure that prevails in the latter, with this underpressure being created by the flow of propellant gas through its internal volume between the jet of the first perforation 11 and the fractionation zone 13. For an equal propellant gas flow rate, the underpressure will be all the higher since the height of the chamber 15 and therefore its volume will be low. The concept is also that by the adjustment of the height of the chamber, the flow rate of the jet that is produced is adjusted.

Purely by way of indication, for a chamber diameter of 8 mm, the height adjustment range will be 0.1 mm to 5 mm based on applications and the integration of the nozzle in a mechanical unit or another element.

The management of the value of the underpressure is important because it makes it possible—within the framework of the use of the spraying nozzle—to draw in a liquid over a distance of 1 to 10 meters with a pressure of 0.5 to 3 bar for a mean consumption of 1 to 500 ml/hour based on the parameterization of the underpressure chamber and the number of liquid intake perforations. For the vaporization, the objective is to use a low-voltage micro-compressor (12 Vcc) for the purpose of acting on the voltage or by a PMW (current variation) for increasing or reducing the flow rate of the aerosol.

It is therefore important to have an efficient underpressure for drawing in a liquid with the lowest possible pressure:

Mean intake level of 20 to 500 mm
Mini-pressure of 15 to 30 mbar for a minimum air flow rate of 1 l/mn
Mean consumption of 0.2 ml/h
Compressor flow rate of 1 l/mn The maximum value is 12 Vcc for a pressure of 400 to 600 mbar and a mean liquid consumption of 1.2 ml/h.

These values are provided for two liquid intakes and a chamber volume on the order of 11 mm$^3$.

The perforation diameter and height influence the underpressure in the chamber and the flow rate of the micro-compressor at the time of start-up.

The tables below show the start-up variation of liquid suction based on the diameter and height of the perforation with the use of a micro-compressor.

| Vaporization 0.6 mm Perforation/1 mm Height | L/mn Compressor Flow Rate | Pressure in mbar | Voltage Vcc |
|---|---|---|---|
| Maximum Pressure | 2 | 570 | 12 |
| Minimum Pressure | 1 | 60 | 4.5 |

| Vaporization 0.7 mm Perforation/1 mm Height | L/mn Compressor Flow Rate | Pressure in mbar | Voltage Vcc |
|---|---|---|---|
| Maximum Pressure | 2 | 560 | 12 |
| Minimum Pressure | 1 | 50 | 4 |

| Vaporization 0.8 mm Perforation/1 mm Height | L/mn Compressor Flow Rate | Pressure in mbar | Voltage Vcc |
|---|---|---|---|
| Maximum Pressure | 2 | 560 | 12 |
| Minimum Pressure | 1.2 | 50 | 4 |

| Vaporization 0.9 mm Perforation/1 mm Height | L/mn Compressor Flow Rate | Pressure in mbar | Voltage Vcc |
|---|---|---|---|
| Maximum Pressure | 2 | 560 | 12 |
| Minimum Pressure | 1 | 50 | 4.2 |

| Vaporization 0.6 mm Perforation/2 mm Height | L/mn Compressor Flow Rate | Pressure in mbar | Voltage Vcc |
|---|---|---|---|
| Maximum Pressure | 2 | 550 | 12 |
| Minimum Pressure | 1 | 60 | 4.5 |

| Vaporization 0.7 mm Perforation/2 mm Height | L/mn Compressor Flow Rate | Pressure in mbar | Voltage Vcc |
|---|---|---|---|
| Maximum Pressure | 2 | 580 | 12 |
| Minimum Pressure | 1 | 30 | 3.8 |

| Vaporization 0.8 mm Perforation/2 mm Height | L/mn Compressor Flow Rate | Pressure in mbar | Voltage Vcc |
|---|---|---|---|
| Maximum Pressure | 2 | 580 | 12 |
| Minimum Pressure | 1 | 20 | 3.5 |

| Vaporization 0.6 mm Perforation/2 mm Height | L/mn Compressor Flow Rate | Pressure in mbar | Voltage Vcc |
|---|---|---|---|
| Maximum Pressure | 2 | 560 | 12 |
| Minimum Pressure | 1 | 30 | 4 |

Advantageously, the nozzle body is formed by two parts 10a, 10b, sealed to one another, with the underpressure chamber 15 being formed between and by these two body parts. This arrangement is particularly advantageous since the height of the chamber 15 can be easily adjusted by moving the two parts away from or toward one another. These two body parts will be sealed to one another by any known means. They can be attached by screws, or by gluing, crimping, welding, etc.

These two body parts can be moved axially relative to one another. The height of the chamber measured in the direction of the AA' axis is limited to 5 mm for a pressure of 6 bar.

In the embodiment that is the object of FIGS. 1, 2, 4, and 7, the perforations 11, 12 of the chamber 15 are formed in the lower part 10a while the fractionation zone 13 is formed in the upper part 10b.

In the embodiment that is the object of FIG. 3, the liquid intake perforations 12 are formed in the upper part 10b.

In the embodiment of FIG. 4 and FIG. 6, the liquid intake perforations 12 are also formed in the part 10a and in the part 10b.

In the embodiment of FIG. 5, the liquid intake perforations 12 are formed in the part 10a while the air intake perforation 11 is formed in the part 10b. In this part 10b, the underpressure chamber 15 is formed. The fractionation zone is formed in the part 10a.

As can be seen in FIGS. 1 to 6, the lower part 10a of each nozzle that is the object of these figures has a male axial cylindrical end fitting shape 16, terminated by a flat surface that is perpendicular to the axis of the body 10, from which surface the chamber 15 is hollowed out. The upper part 10b has a cylindrical cavity 17 of the same diameter as the cylindrical end fitting shape 16. This cavity is engaged in sliding adjustment around the cylindrical end fitting shape 16. The cavity 17 has a flat bottom arranged facing the terminal surface of the cylindrical end fitting shape.

In the embodiment of the nozzle that is the object of FIG. 7, the upper upper part 10b, in the shape of a cylindrical disk, is engaged in a cylindrical housing that is made in the lower part 10a.

The height of the chamber 15 can be determined by wedges in the shape of rings of suitable thicknesses arranged between the two terminal surfaces of the end fitting shape 16 and the cavity 17. After the wedges are installed, the two parts 10a, 10b of the body will be immobilized relative to one another, for example by screws engaged in, on the one hand, transverse perforations made in the body part 10b and in the tappings made in the body part 10a.

The height of the chamber can be determined by construction to prevent the use of wedges.

The cylindrical end fitting 16 is equipped with a groove 16b that is provided for accommodating an O-ring seal 16c. By ensuring the seal between the end fitting 16 and the cavity 17, this arrangement prevents any leak of liquid and propellant gas.

The lower part 10a of the nozzle body is advantageously equipped with an axial end fitting 19 projecting over the lower surface of said part and through which the first perforation passes. This end fitting makes it possible to connect the first perforation to a pipe for distributing propellant gas.

According to a preferred embodiment as shown in FIGS. 2 and 2a, the nozzle body 10 has a continuous distribution groove 18, extending in a circle, into which the different second perforations 12 empty, whereby said groove is designed to be supplied with liquid via a supply cannula that is not shown in this figure. This arrangement makes it possible to simplify the liquid supply of the vaporization nozzle.

As can be seen, this groove 18 is made in the lower body part 10a and is hollowed out in this part from the lower flat surface that the latter exhibits. This flat surface at least at the level of the groove is designed to be covered by a partition to ensure the sealing of the distribution groove 18. The above-mentioned supply cannula will pass all the way through this partition.

Preferably, the fractionation zone 13 is formed by a perforation that empties out into the underpressure chamber 15 and into the axis of the first perforation 11.

The diameter of the fractionation zone 13 is larger than the diameter of the first perforation so that the increase of the flow rate due to the liquid that is drawn in can be easily absorbed. Moreover, the perforation that constitutes the fractionation zone 13 can have a conical widening-out 13a at the level of its opening into the underpressure chamber and facing the first perforation. The angle at the top of this widening-out is between 20 and 60 degrees. This widening-out arrangement promotes putting the underpressure chamber 15 under partial vacuum and increases the efficiency of the fractionation of the liquid.

It should be noted that for an operation of the nozzle under high pressure, the diameter of the fractionation zone will be large enough to prevent this conical widening-out arrangement.

As can be seen in FIGS. 4 and 6, a diffusion bell 14, in communication with the outlet of the fractionation zone 13, can be combined with the nozzle as described.

Preferably, the diffusion bell 14 has at least two radial air intakes 14a, emptying out into its internal volume, whereby said air intakes are uniformly distributed around its axis of symmetry.

Underpressure is created by Venturi effect in each air intake, and air is drawn into the diffusion bell 14. This arrangement increases in a particularly significant manner at the nozzle outlet both as regards the flow rate and the jet speed. As can be seen, these air intakes 14a are formed separated from the fractionation zone and preferably close to the small base of the diffusion bell.

Advantageously, the diffusion bell has a piece for attachment by fitting in the upper part of the nozzle body.

In longitudinal cutaway, FIG. 8 shows a device 2 that is equipped with a nozzle 1 in accordance with the invention.

This device comprises a hollow body 20 that is provided with an end fitting 21 on the collar of a liquid reservoir, a transverse base 22 arranged above the end fitting 21 in which at least one housing 23 is formed that can accommodate, in nested form, a vaporization nozzle 1 that is oriented in the body 20 in such a way as to produce a jet of liquid particles oriented in the axis of the device toward the upper part of the latter.

The transverse base 22 has a pressurized propellant gas intake pipe 22a to which the first perforation 11 of the nozzle 1 corresponds.

In the preferred embodiment, the propellant gas pipe is formed by a blind perforation that is made in the base in a radial manner. Along the longitudinal axis of the body, the base is equipped with a second blind perforation that empties out radially into the first blind perforation. This second blind perforation constitutes the housing 23 and accommodates the connecting piece 19.

In addition, the base will be equipped with at least one perforation that passes through the passage of a supply cannula of the liquid nozzle.

Above the transverse base and above the nozzle 1, the body 20 of this device comprises at least one expansion chamber 24 that is blocked at the upper part by a removable blocking wall 25 that has a vaporization discharge tube 26. The jet that is produced by the nozzle is introduced into this expansion chamber.

The exchange chamber formed in the body is divided transversely by at least one micro-perforated membrane 27 that can allow only particles of a size that is less than a predetermined caliber, for example 3 μm, to pass. This chamber can be equipped with two membranes that are distant from one another and that are passed through successively by vaporization.

Preferably so that the particles that are stopped by the membrane can be evacuated by themselves to the reservoir, the base, in a manner lateral to the nozzle, has through perforations that empty out into the volume of the end fitting 21.

In the embodiment that is the object of FIG. 8, the device 2 comprises only a single expansion chamber 24, but as a variant, it can comprise two axially aligned expansion chambers 24, each of these chambers able to accommodate one or more membranes 27 based on the application envisioned.

This configuration is primarily designed for applications for which the pressure at the vaporization zone outlet is between 0.5 and 3 bar.

A device that comprises several nozzles 1 according to the second embodiment is shown in FIG. 9. These nozzles 1 are mounted on the base 22 so that the conical jets that they produce can be intertwined. According to this embodiment, the body 20 of the device forms a chamber that is open in the upper part above the base. As can be seen, the body of the device close to the upper end of the open chamber has through radial openings 28, uniformly distributed, constituting air intakes. In the lower part, immediately above the base 22, the body 20 can also have other radial openings. Thus, by Venturi effect, air is drawn into this open chamber so as to increase the speed and the flow rate of the jets that are produced.

It is noted in this figure that the part 10b of the body of each nozzle is formed by a common wall that is attached in a removable manner to the base 22.

FIGS. 10 and 11 show in cutaway a disposable vaporization device.

It is possible to see in these figures that the body 20 of the device constitutes a liquid reservoir and that this body is equipped with a connecting piece 201 to a pressurized air source.

In FIG. 10, it is noted that the connecting piece 201 is axial to the cylindrical body of the device and occupies a lower position. This device is provided to be engaged in a housing 30 that is formed in support 3 that accommodates an air compressor 31 that constitutes the pressurized source.

It is observed in this figure that the piece 201 is of the female type and accommodates a male-shaped piece 32 connected to the pressurized air source in nested form. It is noted that this male-shaped piece projects over the bottom of the housing 30.

The expansion chamber 24 is formed by two cones that are reversed relative to one another 240, 241, attached to one another by their large base, with the lower cone 241 forming a funnel for recovery of residual flows. The upper cone 240 is equipped with through perforations 241 for exhaust of the vaporization toward an upper chamber 243 that is formed between said upper cone 240 and an upper cap 244 that comprises the device. The through perforations 241 are formed close to the large base of the upper cone.

This upper cap 244 is equipped with a vaporization discharge piece 245 and is sealed to the body of the device.

Advantageously, the lower cone 241 is extended toward the bottom of the reservoir by a tubular shape 246 that rests on a base 10d that is sealed to the longitudinal body of the lower part 10a of the nozzle. Between this tubular shape 246 and the longitudinal body 10a, there is provided an annular chamber in communication with the reservoir through radial through perforations 247 that are made in this tubular shape, in the lower part. It is also possible to observe that this annular chamber is in communication with the expansion chamber 24.

It is also possible to observe that the base 10d has a radial groove for supply of a liquid intake cannula 12a that comprises the nozzle, whereby this intake cannula is in communication with the corresponding perforation 12. It is possible to observe that this intake cannula 12a is mounted in a longitudinal housing that is formed in the nozzle body part 10a. Around the part 10a, a tubular sheath 10e that rests on the base 10d will be arranged. This tubular sheath is equipped at the lower end with perforations that pass through the passage of liquid to be vaporized.

In this figure, it is possible to see that the device comprises a means for indexing and blocking constituted by a groove 250 in a circumferential arc with a straight T-shaped cross-section in the bottom wall of the device body in which a piece 251 is engaged with the annularly projecting head 252 that is provided to be engaged in the horizontal segment of the T that forms the groove.

FIG. 11 shows another embodiment of a disposable vaporization device that comprises a liquid reservoir that is formed in the device body 20. This device comprises, for example, a nozzle 1 according to FIG. 5. In this figure, it is possible to see that the spray that is formed at the nozzle outlet is oriented toward a lower expansion chamber 24 that is formed above the liquid level contained in the reservoir. The lower wall of this chamber 24 is arranged in a funnel for recovery of residual flows. As can be seen, this funnel has a vertical cannula that sinks into the reservoir. The lower end of this vertical cannula rests on the bottom of the reservoir and has through radial perforations. Liquid intake cannulae 12a, in communication with the perforations 12 of the nozzle, are engaged in the cannula of the funnel and pulse the liquid contained in the body 20 into the lower part of the latter, this body forming a reservoir.

The expansion chamber 24 is in communication with an upper chamber 243 by a through perforation 243a made in the nozzle body, with this chamber comprising a vaporization outlet opening. It is noted in this figure that the air intake 201 is radial to the body of the device.

It goes without saying that this invention can accommodate any arrangements and variants of the field of equivalent techniques without thereby exceeding the scope of this patent.

The invention claimed is:

1. A spraying nozzle formed by a nozzle body comprising:
a first pressurized gas intake perforation that has an inlet opening and an outlet opening,
at least one second perforation that intakes a liquid to be fractionated that has an inlet opening and an outlet opening,
a liquid fractionation zone, that is separate from the first perforation and axially aligned with the first perforation along a geometric axis, wherein said fractionation zone is in communication with the first perforation and second perforation,
several liquid intake perforations, and in that each of these perforations is in communication with the first perforation and with the fractionation zone through a same underpressure chamber formed between said first perforation and the fractionation zone, pressure in which is lower than that of atmospheric pressure,
wherein the propellant gas stream passes through said underpressure chamber along the axis and wherein the diameter of the fractionation zone is larger than the diameter of the first perforation at its opening into the underpressure chamber.

2. The spraying nozzle according to claim 1, wherein the jet of the first perforation at the opening of the latter in the underpressure chamber is axial to said chamber and wherein the jets of the second perforations at the openings of the latter in said chamber are uniformly distributed around the AA' axis.

3. The spraying nozzle according to claim 1, wherein the volume of the underpressure chamber is adjustable.

4. The spraying nozzle according to claim 1, wherein the fractionation zone is formed by a perforation that empties out into the underpressure chamber and into the axis of the first perforation.

5. The spraying according to claim 4, wherein the perforation that constitutes the fractionation zone has a conical widening-out at its opening into the underpressure chamber and facing the first perforation.

6. The spraying nozzle according to claim 1, wherein the nozzle body is formed by two parts that are sealed to one another, with the underpressure chamber being formed between and by the latter.

7. The spraying nozzle according to claim 1, wherein the nozzle body has a continuous distribution groove into which the different second perforations empty out, with said groove being designed to be supplied with liquid by an underpressure cannula.

8. The spraying nozzle according to claim 1, wherein the nozzle body accommodates a diffusion bell of the aerosol that is formed by the propellant gas and by the fractionated liquid, whereby said bell is in communication with the spraying zone.

9. The spraying nozzle according to claim 8, wherein the diffusion bell has at least two air intakes that empty out into its internal volume, whereby said air intakes are uniformly distributed around the axis of symmetry of said bell.

10. The spraying nozzle according to claim 1, wherein the underpressure chamber is equipped with an annular partition, centered relative to the axis, occupying its entire height and dividing it into a central volume through which the carrier gas stream passes and a peripheral annular volume into which the liquid intake perforations empty out, with said annular wall being provided with radial perforations that ensure the communication between the annular volume and the central volume.

11. A vaporization device comprising at least one nozzle according to claim 1.

12. The vaporization device according to claim 11, wherein it has at least one expansion chamber above or below the nozzle.

13. The vaporization device, according to claim 11, wherein it comprises a hollow hardware body that is equipped with an end fitting on the collar of a liquid reservoir, with a transverse base arranged above the end fitting in which at least one housing is formed that can accommodate a spraying nozzle in nested form.

14. The vaporization device according to claim 11, wherein the base has a pressurized propellant gas intake pipe to which the perforation of the nozzle corresponds.

15. The vaporization device according to claim 11, wherein the expansion chamber receives at least one micro-perforated transverse membrane that can allow only liquid particles of sizes less than a predetermined caliber to pass.

16. The vaporization device according to claim 11, wherein it has several nozzles mounted on the base in such a way that the conical jets that they produce are intertwined.

17. The vaporization device according to claim 11, wherein the body constitutes a liquid reservoir, and wherein the vaporization device is disposable.

18. The vaporization device according to claim 17, wherein the expansion chamber is formed by two reversed cones that are attached to one another by their large base, with the lower cone forming a funnel for recovery of residual flows, and the upper cone being equipped with through perforations for exhaust of the vaporization toward an upper chamber that is formed between said upper cone and an upper cap, whereby said upper cap is equipped with a vaporization discharge piece.

19. The vaporization device according to claim 18, wherein the lower cone is extended toward the bottom of the reservoir by a tubular shape that rests on a base that is attached to the longitudinal body of the lower nozzle part and wherein between this tubular shape and the longitudinal body, there is provided an annular chamber that is in communication with the reservoir through radial through perforations made in said tubular shape, in the lower part.

20. The vaporization device according to claim 19, wherein the base has a radial intake groove of a liquid intake cannula that comprises the nozzle, facing each radial perforation, whereby said intake cannula is mounted in a longitudinal housing that is formed in the part of the nozzle body, and wherein a tubular sheath that rests on the base is arranged around the part, whereby said tubular sheath is equipped in the lower end with perforations that pass through the passage of the liquid to be vaporized.

* * * * *